(12) United States Patent
Kim et al.

(10) Patent No.: US 8,263,431 B2
(45) Date of Patent: Sep. 11, 2012

(54) THIAZOLE-BASED SEMICONDUCTOR COMPOUND AND ORGANIC THIN FILM TRANSISTOR USING THE SAME

(75) Inventors: Dong-Yu Kim, Gwangju (KR); Bogyu Lim, Gwangju (KR); Kang-Jun Baeg, Gwangju (KR); Hyung-Gu Jeong, Gwangju (KR); Seung-Hwan Oh, Gwangju (KR); Hong-Ju Park, Gwangju (KR)

(73) Assignee: Gwangju Institute of Sciences and Technology, Gwangju (KR)

( * ) Notice: Subject to any disclaimer, the term of this patent is extended or adjusted under 35 U.S.C. 154(b) by 46 days.

(21) Appl. No.: 13/012,388

(22) Filed: Jan. 24, 2011

(65) Prior Publication Data

US 2011/0177653 A1     Jul. 21, 2011

Related U.S. Application Data

(62) Division of application No. 12/325,553, filed on Dec. 1, 2008, now Pat. No. 7,897,963.

(30) Foreign Application Priority Data

Nov. 30, 2007    (KR) .................. 10-2007-0123143

(51) Int. Cl.
     *H01L 51/40*      (2006.01)
(52) U.S. Cl. ............... 438/99; 257/40; 257/E51.001; 548/153
(58) Field of Classification Search ............ 257/40, 257/E51.001; 548/153; 438/99
See application file for complete search history.

(56) References Cited

U.S. PATENT DOCUMENTS

| | | | |
|---|---|---|---|
| 7,709,829 B2 | 5/2010 | Tanaka et al. | |
| 2004/0124410 A1 | 7/2004 | Lee et al. | |
| 2006/0006379 A1 | 1/2006 | Lee et al. | |
| 2006/0151779 A1 | 7/2006 | Lee et al. | |
| 2007/0128764 A1 | 6/2007 | Tomino et al. | |
| 2008/0012009 A1 | 1/2008 | Hashizume et al. | |
| 2008/0087884 A1 | 4/2008 | Doi | |
| 2008/0128684 A1 | 6/2008 | Kim et al. | |
| 2008/0191198 A1 | 8/2008 | Han et al. | |
| 2008/0241594 A1 | 10/2008 | Doi | |
| 2008/0251784 A1 | 10/2008 | Tanaka et al. | |
| 2009/0072224 A1 | 3/2009 | Aramaki et al. | |
| 2009/0121216 A9 | 5/2009 | Han et al. | |

OTHER PUBLICATIONS

Shinji Ando, Jun-ichi Nishida, Youji Inoue, Shizuo Tokito and Yoshiro Yamashita J. Mater. Chem., 2004,14, 1787-1790.*
Peter Zahradnik, Peter Magdolen, Pavol Zahradnik, Thiazolo[4,5-d]thiazole—a new domain for potential optoelectronic application, Tetrahedron Letters, vol. 51, Issue 44, Nov. 3, 2010, pp. 5819-5821.*

* cited by examiner

*Primary Examiner* — Jarrett Stark
(74) *Attorney, Agent, or Firm* — Occhiuti Rohlicek & Tsao LLP (57) ABSTRACT

Provided are an organic semiconductor compound using thiazole, and an organic thin film transistor having an organic semiconductor layer formed of the organic semiconductor compound using thiazole. The novel organic semiconductor compound including thiazole has liquid crystallinity and excellent thermal stability, and thus is provided to form an organic semiconductor layer in the organic thin film transistor. To this end, a silicon oxide layer is formed on a silicon substrate, and an organic semiconductor layer including thiazole is formed on the silicon oxide layer. In addition, source and drain electrodes are formed on both edge portions of the organic semiconductor layer. The organic thin film transistor using the organic semiconductor layer has an improved on/off ratio and excellent thermal stability. Also, a solution process can be applied in its manufacture.

4 Claims, 4 Drawing Sheets

THIAZOLE-BASED SEMICONDUCTOR COMPOUND AND ORGANIC THIN FILM TRANSISTOR USING THE SAME

CROSS-REFERENCE TO RELATED APPLICATION

This application is a divisional application of U.S. application Ser. No. 12/325,553, filed Dec. 1, 2008, which claims priority to Korean Application 10-2007-0123143 filed Nov. 30, 2007. Contents of the prior applications are incorporated herein by reference.

BACKGROUND OF THE INVENTION

1. Field of the Invention

The present invention relates to an organic semiconductor compound and an organic thin film transistor using the same, and more particularly, to an organic semiconductor compound including thiazole, and an organic thin film transistor using the same which can be applied in a solution process and have an improved on/off ratio.

2. Description of the Related Art

Organic thin film transistors have several advantages which have made them a focus of active research and development. In particular, an organic thin film transistor can be fabricated in a simple process and at low cost, and can be easily applied to a flexible electronic circuit substrate that is resistant to breakage due to impact, and can be bent and folded.

In addition, compared to a conventional thin film transistor using amorphous silicon and polysilicon, an organic thin film transistor can be fabricated in a simple process and at low cost, and has excellent compatibility with substrates on which other electronic parts are mounted. It is for these reasons that organic thin film transistors have been widely researched in recent times.

However, for an organic thin film transistor to perform well, it should have a high on/off ratio and high charge mobility.

Also, an organic semiconductor forming the organic thin film transistor may be classified as small molecule semiconductor or polymer semiconductor depending on its molecular weight.

Generally, small molecule semiconductor can be easily purified to almost perfectly remove impurities and thereby obtain excellent electrical properties. But, it cannot be applied in a solution process such as spin coating and printing, and thus a thin film should be formed by vacuum deposition using an expensive vacuum device.

On the other hand, polymer semiconductor is difficult to thoroughly purify and its impurities cannot be perfectly removed. But, it has high thermal stability and can be applied in a solution process such spin coating and printing, and this it is preferable for low-cost processing and mass production.

Therefore, there is need to develop an organic semiconductor compound simultaneously having the advantages of both small molecule semiconductor and polymer semiconductor.

SUMMARY OF THE INVENTION

The present invention is directed to an organic semiconductor compound that has an improved on/off ratio and excellent thermal stability, and can be used in an organic thin film transistor to which a solution process can be applied.

The present invention is also directed to a method of fabricating an organic thin film transistor using the organic semiconductor compound.

The present invention is also directed to an organic thin film transistor using the organic semiconductor compound.

According to an embodiment of the present invention, a thiazole-based organic semiconductor compound is represented by Formula 1 below:

[Formula 1]

Here, $R_1$, $R_2$, $R_3$ and $R_4$ are independently selected from a group consisting of hydrogen, a C1-C25 alkyl group, a C1-C25 alkoxy group, and a C6-C30 aryl group substituted with C1-C25 alkyl and alkoxy groups.

In Formula 1, X and Y are substituents or substituent groups identically or independently selected from a group consisting of -continued wherein Z1 is an independently single- or multi-substituted substituent selected from a group consisting of hydrogen, a hydroxyl group, a substituted or unsubstituted methyl group, a carbonyl group, an amino group, a substituted or unsubstituted C1-C30 alkyl amino group, a substituted or unsubstituted C1-C30 aryl amino group, a substituted or unsubstituted heteroaryl amino group, a cyano group, a halogen atom, a substituted or unsubstituted C1-C30 alkyl group, a substituted or unsubstituted C3-C30 cycloalkyl group, a substituted or unsubstituted C1-C30 alkoxy group, a substituted or unsubstituted C6-C30 aryl group, a substituted or unsubstituted C6-C30 aryl alkyl group, a substituted or unsubstituted C2-C30 heteroaryl group, and a substituted or unsubstituted C2-C30 heterocyclic group.

R5, R6, R7 and R8 are selected from a group consisting of hydrogen, a C1-C25 ethylene oxide group, a C1-C25 alkyl group, a C1-C25 fluorinated alkyl group, a C1-C25 alkoxy group, a C1-C25 alkylene oxide group, a C1-C25 polydimethylsiloxane group, a C1-C25 alkylene sulfide group, and a C1-C25 ethylene sulfide group.

According to another embodiment of the present invention, a method of fabricating an organic thin film transistor includes: preparing a silicon substrate; forming an insulating layer using silicon oxide on the silicon substrate; forming an organic semiconductor layer using a compound of Formula 1 on the insulating layer; and forming source and drain electrodes on the organic semiconductor layer.

Here, the organic semiconductor layer may be formed by depositing the material of Formula 1 under high vacuum.

Alternatively, the organic semiconductor layer may be formed by coating the material of Formula 1 dissolved in a solution.

According to still another embodiment of the present invention, an organic thin film transistor includes: a silicon substrate; an insulating layer formed of silicon oxide on the silicon substrate; an organic semiconductor layer formed of the material of Formula 1 on the insulating layer; and electrode layers formed on the organic semiconductor layer.

Here, the organic semiconductor layer may be formed by depositing the material of Formula 1 under high vacuum.

Alternatively, the organic semiconductor layer may be formed by coating the material of Formula 1 dissolved in a solution.

BRIEF DESCRIPTION OF THE DRAWINGS

These and/or other objects, aspects and advantages of the invention will become apparent and more readily appreciated from the following description of exemplary embodiments and the accompanying drawings, in which.

DETAILED DESCRIPTION OF THE INVENTION

Reference will now be made in detail to exemplary embodiments of the present invention, examples of which are shown in the accompanying drawings.

However, it should be understood that the present invention is not limited to the described exemplary embodiments, but includes various modifications, equivalents and alternatives.

In this description, the terms "first" and "second" may be used to distinguish similar elements from one another, however these terms should not be construed as limiting the elements in any way.

Hereinafter, exemplary embodiments of the present invention will be described in more detail with reference to the accompanying drawings. When the same element appears in different drawings, it will always be denoted by the same reference numeral and it will only be described once. It should be clear that these embodiments are provided only to explain the present invention, not to limit its scope.

A thiazole-based organic semiconductor compound according to the present invention is represented by Formula 1:

[Formula 1]

In Formula 1, R1, R2, R3 and R4 are identically or independently selected from a group consisting of hydrogen, a C1-C25 alkyl group, a C1-C25 alkoxy group, and a C6-C30 aryl group substituted with C1-C25 alkyl and alkoxy groups.

In Formula 1, X and Y are substituents or substituent groups identically or independently selected from a group consisting of wherein Z1 is an independently single- or multi-substituted substituent selected from a group consisting of hydrogen, a hydroxyl group, a substituted or unsubstituted methyl group, a carbonyl group, an amino group, a substituted or unsubstituted C1-C30 alkyl amino group, a substituted or unsubstituted C1-C30 aryl amino group, a substituted or unsubstituted heteroaryl amino group, a cyano group, a halogen atom, a substituted or unsubstituted C1-C30 alkyl group, a substituted or unsubstituted C3-C30 cycloalkyl group, a substituted or unsubstituted C1-C30 alkoxy group, a substituted or unsubstituted C6-C30 aryl group, a substituted or unsubstituted C6-C30 aryl alkyl group, a substituted or unsubstituted C2-C30 heteroaryl group, and a substituted or unsubstituted C2-C30 heterocyclic group.

R5, R6, R7 and R8 are independently selected from a group consisting of hydrogen, a C1-C25 ethylene oxide group, a C1-C25 alkyl group, a C1-C25 fluorinated alkyl group, a C1-C25 alkoxy group, a C1-C25 alkylene oxide group, a C1-C25 polydimethylsiloxane group, a C1-C25 alkylene sulfide group, and a C1-C25 ethylene sulfide group.

EXAMPLE 1

Synthesis of Compound of Formula 2

[Formula 2]

[Scheme 1]

A compound of Formula 2 was synthesized according to Scheme 1. The compound of Formula 2 is an example of Formula 1. A compound (1) is commercially available from the Aldrich Company.

200 ml of THF dried over sodium was cooled to 0° C., and then 15.18 ml (138 mmol) of TiCl$_4$ was slowly added to the THF while stirring. After 15 minutes, 18 g (276 mmol) of zinc was added, and then the resulting mixture was heated while stirring for 1 hour. After the mixture was cooled to 0° C., 13 g (115.92 mmol) of the compound (1) was dissolved in 50 ml of the dried THF, and the resulting mixture was heated while stirring for 3 hours. After that, the mixture was slowly cooled to room temperature, and 50 ml of ice water was added to terminate the reaction. Precipitates were filtered and recrystallized using cyclone hexane to obtain a compound (2) (yield: 65%).

14 ml of DMF was stirred to be well mixed with 1.5 ml (16.5 mmol) of POCl$_3$ at 0° C., and the resulting mixture was slowly added while stirring to a solution made from dissolving 2.74 g (14.25 mmol) of the compound (2) in 40 ml of DMF at 0° C. After that, the resulting solution was slowly heated to room temperature and stirred at 50° C. for 3 hours. The resulting solution was neutralized using 100 ml of 1M NaOH aqueous solution, extracted using benzene, and then purified by a silica column apparatus to obtain a compound (3) (yield: 70.08%).

2.20 g (10 mmol) of the compound (3) and 0.541 g (4.5 mmol) of dithiooxamide were dissolved in 20 ml of 1,2- dichlorobenzene and stirred and heated for 24 hours. Afterwards, the solution was cooled to room temperature, precipitated using 100 ml of ethanol, and filtered. The filtered material was washed with ethanol several times and purified by a silica column apparatus to obtain the compound of Formula 2 (yield: 22%).

Figure 1:
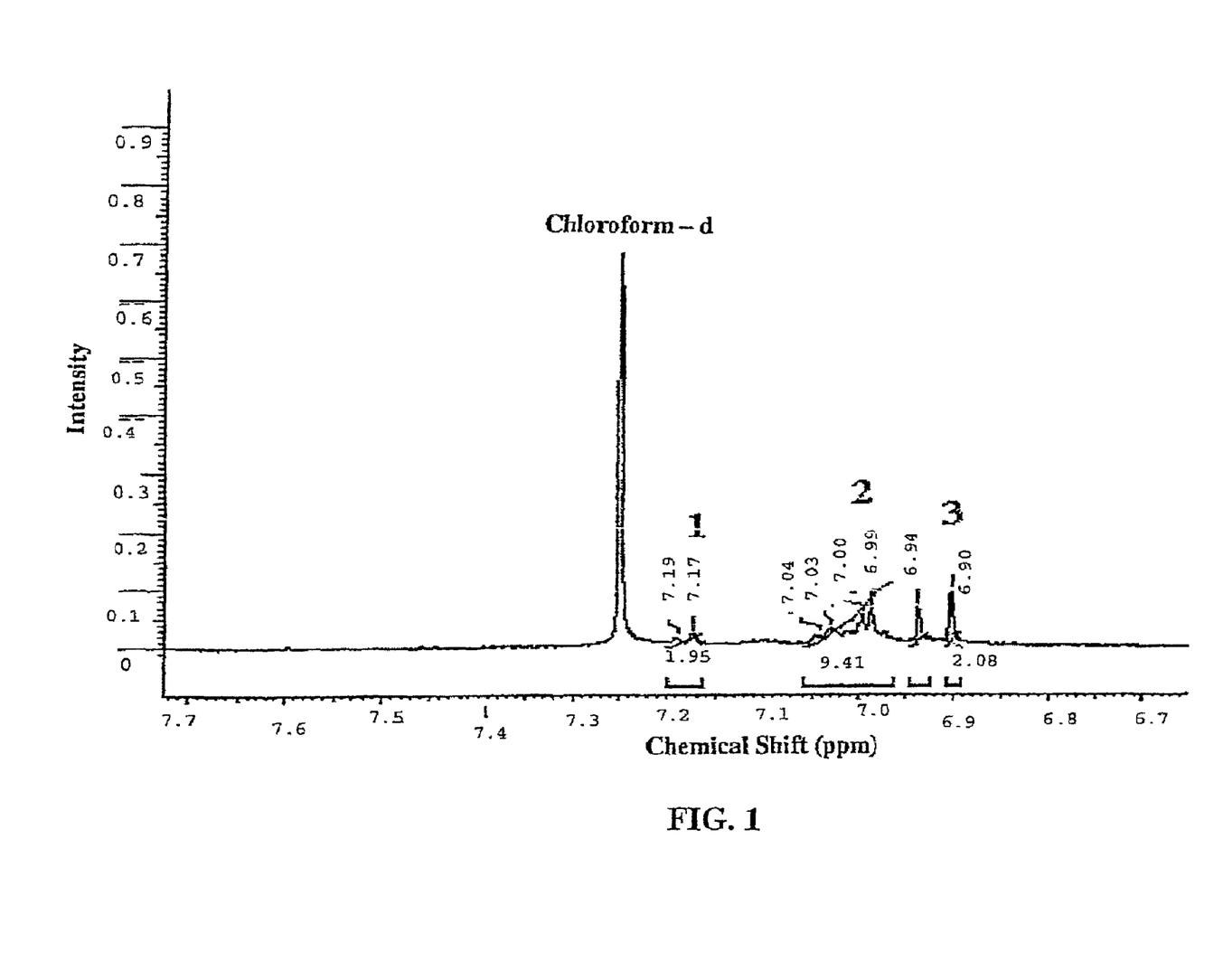
FIG. 1 is a 1H-NMR graph of an organic semiconductor compound represented by Formula 2 of the present invention.
Figure 2:
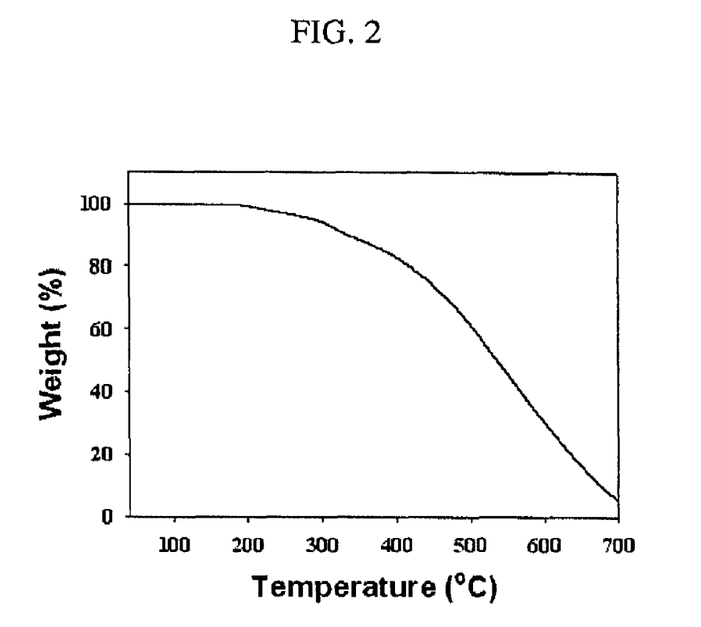
FIG. 2 is a thermogravimetric graph of the organic semiconductor compound represented by Formula 2 of the present invention.
Figure 3:
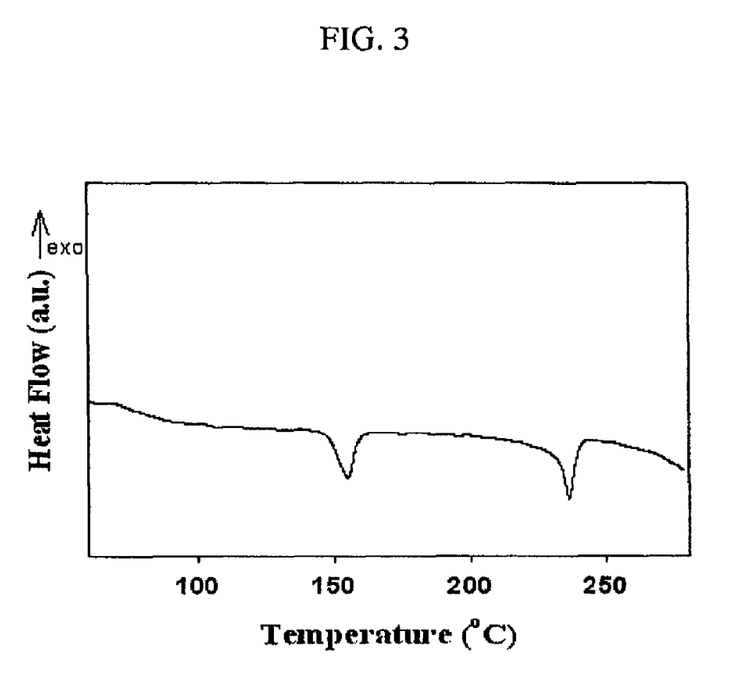
FIG. 3 is a differential scanning calorimetry graph of the organic semiconductor compound represented by Formula 2 of the present invention.
Figure 4:
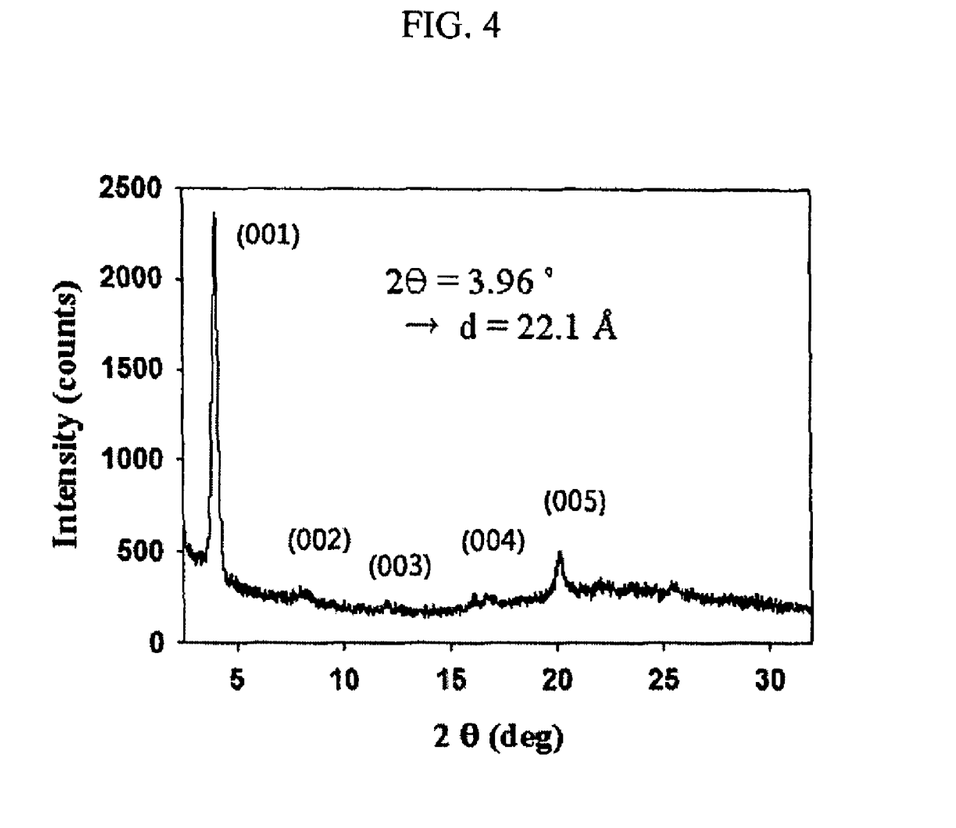
FIG. 4 is an x-ray diffraction graph of the organic semiconductor compound represented by Formula 2 of the present invention.

A structure of the compound of Formula 2 was analyzed by 1H-NMR shown in FIG. 1 and mass spectrometry. Referring to FIG. 2, which shows thermogravimetric analysis results of the synthesized compound of Formula 2, 5% mass reduction of the synthesized compound of Formula 2 is detected at 302° C. This indicates that the synthesized compound of Formula 2 has excellent thermal stability. Referring to FIG. 3, which shows differential scanning calorimetry results, the synthesized compound of Formula 2 has phase change points at 155° C. and 240° C. In FIG. 3, which shows the differential scanning calorimetry results, two different phase change temperatures are observed, which indirectly indicates that the compound of Formula 2 has liquid crystallinity. Referring to FIG. 4, which shows an X-ray diffraction graph of an organic semiconductor represented by Formula 2, it can be noted that the organic semiconductor represented by Formula 2 has 5 peaks, which indicates that it has crystallinity.

A method of fabricating an organic thin film transistor having an organic semiconductor layer formed of the compound of Formula 1 according to the present invention includes forming a silicon substrate, forming an insulating layer using silicon dioxide, forming an organic semiconductor layer using the compound of Formula 1, and forming source and drain electrodes.

EXAMPLE 2

Fabrication of Organic Thin Film Transistor

The following description concerns an example of a method of fabricating an organic thin film transistor having an organic semiconductor layer formed of the compound of Formula 2, which is an example of the compound of Formula 1.

Figure 6:
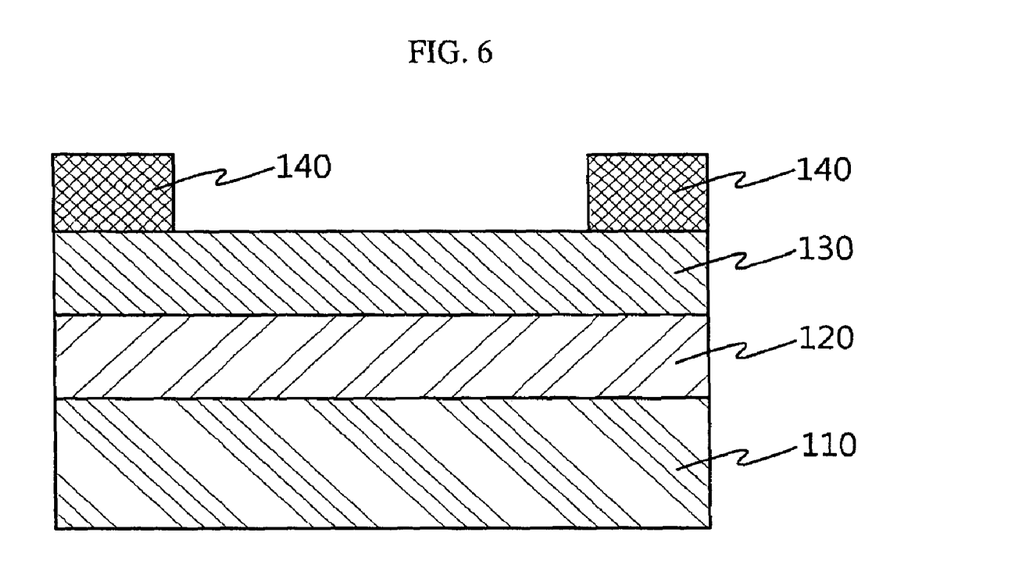
FIG. 6 is a cross-sectional view of an organic thin film transistor having an organic semiconductor layer formed of the organic semiconductor compound represented by Formula 1.

First, a silicon substrate 110 is provided. The silicon substrate 110 may be doped with an n-type dopant. In addition, the n-type silicon substrate serves as a gate electrode of an organic thin film transistor to be formed later.

Subsequently, an insulating layer 120 was formed by thermally growing silicon oxide to a thickness of 300 nm on the substrate. The insulating layer 120 may be formed by various methods except for thermal growth. That is, the insulating layer 120 may be formed by chemical vapor deposition, physical vapor deposition or atomic layer deposition.

Subsequently, the compound of Formula 2 was deposited under vacuum, or dissolved in a solution such as chlorobenzene and then spin-coated, thereby forming an organic semiconductor layer 130 to a thickness of 50 nm.

Finally, 30 ml of gold was deposited on the organic semiconductor layer 130 under vacuum, thereby forming source and drain electrodes 140.

Figure 5:
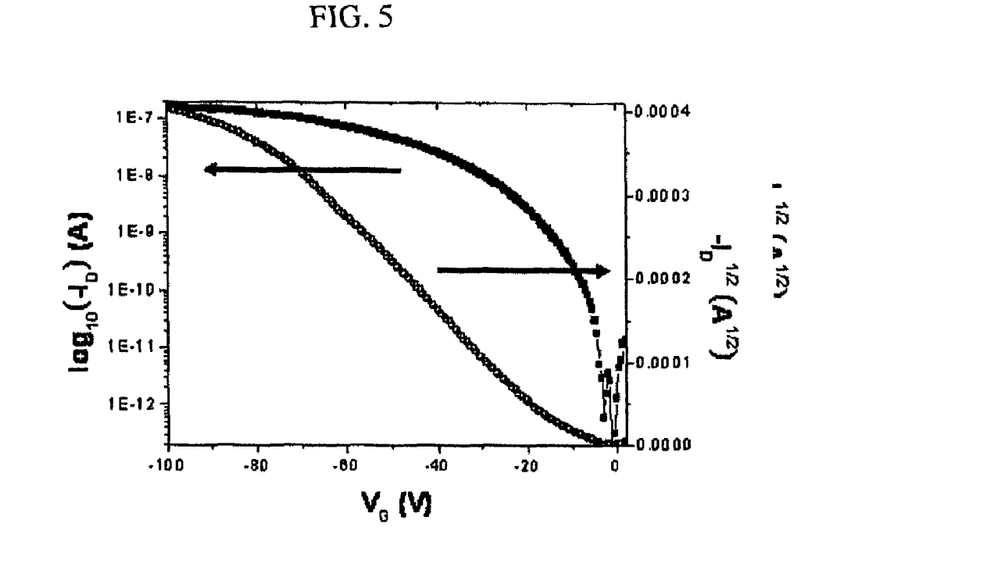
FIG. 5 is a graph showing electrical properties of an organic thin film transistor device using the organic semiconductor compound represented by Formula 2 of the present invention.

Electrical properties of the organic thin film transistor fabricated by the above-described process was analyzed as shown in FIG. 5 using an apparatus for analyzing semiconductor characteristics. Referring to FIG. 5, the organic thin film transistor of this Example exhibits an excellent on/off ratio of more than $10^6$.

FIG. 6 is a cross-sectional view of an organic thin film transistor having an organic semiconductor layer formed of the compound of Formula 1.

Referring to FIG. 6, the organic thin film transistor of this Example is formed of a silicon substrate 110, an insulating layer 120, an organic semiconductor layer 130 and electrode layers 140.

The insulating layer 120 is formed on the silicon substrate 110 serving as a gate electrode. The insulating layer 120 is formed of silicon oxide, and the organic semiconductor layer 130 is formed on the insulating layer 120. The organic semiconductor layer 130 is formed of the organic compound represented by Formula 2. In addition, the electrode layers 140 are formed of a metallic material on edge portions of the organic semiconductor layer 130. The electrode layers serve as source and drain electrodes, respectively. Preferably, the electrode layers include gold. However, it can be clearly understood by those skilled in the art that any one of the conductors formed on the organic semiconductor layer by an appropriate method can be used for an electrode layer.

The substrate 110 is formed of n-type silicon and functions as a gate electrode. The insulating layer 120 is formed of silicon oxide which is thermally grown to a thickness of 300 nm on the substrate 110. The organic semiconductor layer 130 is formed of the compound of Formula 1. For example, the organic semiconductor layer may be formed to a thickness of 50 nm by depositing the compound of Formula 2 under vacuum, or dissolving the compound of Formula 2 in a solution such as chlorobenzene and spin-coating the resulting solution. The electrode layers 140 are formed by depositing 30 ml of gold on the organic semiconductor layer under vacuum to serve as source and drain electrodes.

When a novel thiazole-based organic semiconductor compound of the present invention is used for an organic thin film transistor, an on/off ratio and thermal stability can be improved, and a solution process can be adopted.

While exemplary embodiments of the present invention have been shown and described in detail, it will be appreciated by those skilled in the art that various changes can be made to these embodiments without departing from the principles and spirit of the invention, the scope of which is defined by the claims and their equivalents.

What is claimed is:

1. A thiazole-based organic semiconductor compound represented by Formula 1:

[Formula 1]

Here, R1, R2, R3 and R4 are selected from a group consisting of hydrogen, a C1-C25 alkyl group, a C1-C25 alkoxy group, and a C6-C30 aryl group substituted with C1-C25 alkyl and alkoxy groups, and X and Y are substituents or substituent groups identically or independently selected from a group consisting of wherein Z1 is an independently single- or multi-substituted substituent selected from a group consisting of hydrogen, a hydroxyl group, a substituted or unsubstituted methyl group, a carbonyl group, an amino group, a substituted or unsubstituted C1-C30 alkyl amino group, a substituted or unsubstituted C1-C30 aryl amino group, a substituted or unsubstituted heteroaryl amino group, a cyano group, a halogen atom, a substituted or unsubstituted C1-C30 alkyl group, a substituted or unsubstituted C3-C30 cycloalkyl group, a substituted or unsubstituted C1-C30 alkoxy group, a substituted or unsubstituted C6-C30 aryl group, a substituted or unsubstituted C6-C30 aryl alkyl group, a substituted or unsubstituted C2-C30 heteroaryl group, and a substituted or unsubstituted C2-C30 heterocyclic group; and R5, R6, R7 and R8 are selected from a group consisting of hydrogen, a C1-C25 ethylene oxide group, a C1-C25 alkyl group, a C1-C25 fluorinated alkyl group, a C1-C25 alkoxy group, a C1-C25 alkylene oxide group, a C1-C25 polydimethylsiloxane group, a C1-C25 alkylene sulfide group, and a C1-C25 ethylene sulfide group.

2. A method of fabricating an organic thin film transistor, comprising:
preparing a silicon substrate;
forming an insulating layer using silicon oxide on the silicon substrate;
forming an organic semiconductor layer using a compound of Formula 1 on the insulating layer; and
forming source and drain electrodes on the organic semiconductor layer,

[Formula 1]

wherein R1, R2, R3 and R4 are independently selected from a group consisting of hydrogen, a C1-C25 alkyl group, a C1-C25 alkoxy group, and a C6-C30 aryl group substituted with C1-C25 alkyl and alkoxy groups, and X and Y are substituents or substituent groups identically or independently selected from a group consisting of wherein Z1 is an independently single- or multi-substituted substituent selected from a group consisting of hydrogen, a hydroxyl group, a substituted or unsubstituted methyl group, a carbonyl group, an amino group, a substituted or unsubstituted C1-C30 alkyl amino group, a substituted or unsubstituted C1-C30 aryl amino group, a substituted or unsubstituted heteroaryl amino group, a cyano group, a halogen atom, a substituted or unsubstituted C1-C30 alkyl group, a substituted or unsubstituted C3-C30 cycloalkyl group, a substituted or unsubstituted C1-C30 alkoxy group, a substituted or unsubstituted C6-C30 aryl group, a substituted or unsubstituted C6-C30 aryl alkyl group, a substituted or unsubstituted C2-C30 heteroaryl group, and a substituted or unsubstituted C2-C30 heterocyclic group; and R5, R6, R7 and R8 are selected from a group consisting of hydrogen, a C1-C25 ethylene oxide group, a C1-C25 alkyl group, a C1-C25 fluorinated alkyl group, a C1-C25 alkoxy group, a C1-C25 alkylene oxide group, a C1-C25 polydimethylsiloxane group, a C1-C25 alkylene sulfide group, and a C1-C25 ethylene sulfide group.

3. The method according to claim 2, wherein the forming of the organic semiconductor layer includes depositing the compound of Formula 1 under high vacuum.

4. The method according to claim 2, wherein the forming of the organic semiconductor layer includes coating the compound of Formula 1 dissolved in a solution.

* * * * *